(12) United States Patent
Chen et al.

(10) Patent No.: US 12,263,460 B2
(45) Date of Patent: Apr. 1, 2025

(54) REACTOR SYSTEM FOR THE PRODUCTION OF HIGH VALUE CHEMICAL PRODUCTS

(71) Applicant: SABIC Global Technologies B.V., Bergen op Zoom (NL)

(72) Inventors: Lei Chen, Sugar Land, TX (US); Sreekanth Pannala, Sugar Land, TX (US); David West, Bellaire, TX (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 133 days.

(21) Appl. No.: 18/313,527

(22) Filed: May 8, 2023

(65) Prior Publication Data

US 2023/0271157 A1   Aug. 31, 2023

Related U.S. Application Data

(63) Continuation of application No. 17/626,951, filed as application No. PCT/US2021/040411 on Jul. 6, 2021, now Pat. No. 11,679,370.

(Continued)

(51) Int. Cl.
*C07C 5/327* (2006.01)
*B01J 4/00* (2006.01)
(Continued)

(52) U.S. Cl.
CPC ............ *B01J 19/245* (2013.01); *B01J 4/001* (2013.01); *B01J 6/008* (2013.01); *B01J 19/2445* (2013.01);
(Continued)

(58) Field of Classification Search
CPC . B01J 19/245; B01J 4/001; B01J 6/008; B01J 19/2445; B01J 2204/002; C07C 5/327
See application file for complete search history.

(56) References Cited

U.S. PATENT DOCUMENTS 2,508,120 A   5/1950  Lonngren
2,644,744 A   7/1953  Hartwig et al.
(Continued)

FOREIGN PATENT DOCUMENTS

CN   104540583 A   12/2010
CN   102361687 A   2/2012
(Continued)

OTHER PUBLICATIONS

International Search Report and Written Opinion dated Oct. 13, 2021 in counterpart International PCT Application No. PCT/US2021/040411.

(Continued)

*Primary Examiner* — Kaity V Chandler
(74) *Attorney, Agent, or Firm* — Grady K. Bergen; Griggs Bergen LLP; Robert E. Holthus

(57) ABSTRACT

The invention is directed to a chemical reactor (100) having (a) two or more gas reactor elements (12) with each gas reactor element (12) having (i) a first reaction chamber (38), and (ii) a feed assembly unit (36), (b) a second reaction chamber (20) coupled with each of the two or more gas reactor elements (12) and configured to independently receive two or more product streams from the two or more gas reactor elements (12); and optionally, (c) a gas converging section (40) located downstream to the second reaction chamber (20). The invention is further directed to a method of producing chemical products using the chemical reactor (100) of the present invention.

20 Claims, 9 Drawing Sheets

Related U.S. Application Data

(60) Provisional application No. 63/048,207, filed on Jul. 6, 2020.

(51) Int. Cl.
 *B01J 6/00* (2006.01)
 *B01J 19/24* (2006.01)

(52) U.S. Cl.
 CPC ......... *C07C 5/327* (2013.01); *B01J 2204/002* (2013.01)

(56) References Cited

U.S. PATENT DOCUMENTS

| | | |
|---|---|---|
| 3,498,753 A | 3/1970 | Hokari et al. |
| 2007/0249738 A1 | 10/2007 | Haynes et al. |
| 2009/0324479 A1 | 12/2009 | Kulkarni et al. |
| 2018/0111886 A1 | 4/2018 | Gattupalli et al. |
| 2018/0191009 A1 | 7/2018 | Palumbo et al. |
| 2021/0046440 A1 | 2/2021 | Pannala et al. |

FOREIGN PATENT DOCUMENTS

| | | |
|---|---|---|
| CN | 105771868 A | 7/2016 |
| CN | 107530666 A | 1/2018 |
| CN | 108671876 A | 10/2018 |
| CN | 109482129 A | 3/2019 |
| CN | 111867717 A | 10/2020 |
| CN | 113195092 A | 7/2021 |
| EP | 0593171 A1 | 4/1994 |
| WO | WO2016209648 A1 | 12/2016 |
| WO | WO2019173570 A1 | 9/2019 |
| WO | WO2020086681 A2 | 4/2020 |

OTHER PUBLICATIONS

Extended European Search Report in counterpart European Patent Application No. EP21837820.6, dated Jun. 9, 2022, pp. 1-10.
Office Action in counterpart Chinese Patent Application No. CN202180005403.3, with English translation, dated Jun. 21, 2022, pp. 1-9.

REACTOR SYSTEM FOR THE PRODUCTION OF HIGH VALUE CHEMICAL PRODUCTS

CROSS-REFERENCE TO RELATED APPLICATIONS

This application is a continuation of U.S. patent application Ser. No. 17/626,951, filed Jan. 13, 2022, which is a national stage application under 35 U.S.C. § 371 of International PCT Application No. PCT/US2021/040411, filed Jul. 6, 2021, which claims the benefit of U.S. Provisional Application No. 63/048,207, filed Jul. 6, 2020, each of which is incorporated herein by reference in its entirety.

TECHNICAL FIELD

The present invention is directed to the field of chemical reactors and in particular to the design of such chemical reactors which are suitable for the production of high value chemical products.

BACKGROUND

Cost effective production of commercially high value chemicals such as olefins, and alkynes have been a subject of extensive research for decades for the chemical industry. Processes which are commonly used in the industry to produce such high value chemicals include steam cracking and pyrolysis of long-chain hydrocarbons using traditional crackers or pyrolysis reactors. Conventionally, steam crackers have been the industry's go-to reactors to break long-chain hydrocarbons and modify smaller alkanes (i.e., naphtha, butane, ethane) into commercially high value chemicals. In such crackers, hydrocarbon feedstocks are typically fed into a furnace with steam and converted into smaller olefins. Typically, the cracking process is operated at high temperatures (i.e., from 700° C. to 900° C.) and has residence times of around 100 to 500 milliseconds. Although the process of hydrocarbon cracking and pyrolysis, have been optimized over the last five decades there are still significant disadvantages and operational limitations, which are required to be overcome. Some of these deficiencies include 1) heat losses and process complexities associated with separate exothermic (e.g., combustion in the furnace) and endothermic steps (e.g., cracking in the process tubes), 2) presence of inert compounds, which adversely affects process efficiency, 3) metallurgical limitations of the reactor components, when such components are subjected to extreme reactor severity, 4) coke deposition, leading to plugging of the reactors resulting in increased capital and operational expenses, 5) lack of feedstock flexibility, as commercial crackers/pyrolysis systems, are typically optimized for only certain feedstock characteristics.

In another previous development, a single-stage combustion pyrolysis method to produce acetylene was developed by BASF, which is described in U.S. Pat. No. 5,789,644. This process has been commercialized at 50 kTA scale using multiple reactors in Germany and the U.S. In this process, natural gas serves for the hydrocarbon feed and pure oxygen serves as the oxidant to generate heat, which is critical for acetylene production. The two streams are premixed in a diffuser, and the premixed fuel rich gas is combusted using a burner block through partial oxidation. A major disadvantage of such a design is the flashback risks of the premixed flame under various feedstock and operating conditions, as well as the plurality of burners used, which increases the total cost of operation, difficulties in heat control, excessive coking, and low carbon yield toward olefin product. Furthermore, while acetylene used to be the building block for chemicals, over the last six to seven decades olefins have become the building blocks of the chemical industries and there is a desire to directly produce olefins rather than the indirect hydrogenation route using acetylene.

Some or all of the drawbacks described above regarding the operation of traditional crackers and pyrolysis reactors, are addressed by way of the teachings provided in U.S. Pat. No. 11,020,719, which describes a pyrolysis reactor for the conversion of hydrocarbons to alkynes. Yet another solution to overcome some or all of the drawbacks of traditional crackers have also been described in International Publication No. WO2020/086681A2. Although productivity and conversion efficiency of the reactor system described in U.S. Pat. No. 11,020,719 or in International Publication No. WO2020/086681A2, are promising, there is a scope to further increase the capacity while maintaining the selectivity and hydrocarbon conversion by suitable modification of the designs of existing chemical reactor systems. Particularly, it was observed that as dimensions of the single reactor element described in U.S. Pat. No. 11,020,719 were increased beyond a particular scale, for the purpose of scaling up the production, the C2+ product selectivity and yield, were found to be negatively affected because of increased mixing time scale.

Thus, for the foregoing reasons, there remains a need for developing a chemical reactor for the conversion of hydrocarbons to commercially high value chemicals at high productivity and improved process efficiency while addressing one or more drawbacks typically associated with conventional crackers or pyrolysis reactor systems.

BRIEF SUMMARY

The invention is directed to a chemical reactor comprising: (a) two or more gas reactor elements, wherein each of the gas reactor element comprises: (i) a first reaction chamber having (1) an upstream end, and (2) a downstream end, wherein the first reaction chamber is defined by a first reactor wall surrounding a first central longitudinal axis, wherein the first reaction chamber has an opening located at the downstream end of the first reaction chamber; (ii) a feed assembly unit, surrounding the first central longitudinal axis and operably connected with the first reaction chamber, wherein the feed assembly unit, comprises: 1) a mixing chamber defined by one or more feed assembly walls surrounding the first central longitudinal axis, wherein the mixing chamber is operably connected to the upstream end of the first reaction chamber and at least one feed assembly wall is operably connected with the first reactor wall; and 2) two or more feed inlet flow spaces, each in fluid communication with the mixing chamber, and are configured to inject a feed stream into the mixing chamber at radial and/or non-radial direction with regard to the first central longitudinal axis; (b) a second reaction chamber coupled with each of the two or more gas reactor elements and configured to independently receive two or more product streams from the two or more gas reactor elements, wherein the second reaction chamber has (i) a second central longitudinal axis, (ii) a downstream end, and (iii) an upstream end, and further wherein the second reaction chamber is defined by: (1) a second reactor wall surrounding the second central longitudinal axis, and extending from the upstream end of the second reaction chamber to the downstream end of the second reaction chamber; and (2) a bottom plate extending across the second central longitudinal axis, and located at the upstream end of the second reaction chamber, wherein the bottom plate is joined perimetrically with the second reactor wall; further wherein, the opening of each of the first reaction chamber forms a second reaction chamber inlet located at the upstream end of the second reaction chamber so that the first reaction chamber is in fluid communication with the second reaction chamber; and (3) one or more product outlets operably connected with the downstream end of the second reaction chamber; wherein, for each of the two or more gas reactor elements, the first reaction chamber has a length ranging from 1 R to 10 R, wherein 'R' is a radius of a circle, with the plane of the circle being oriented perpendicular to the first central axis, and the circle having a maximum radius that can be inscribed within the opening located at the downstream end of the first reaction chamber, and further wherein, the angle formed between the first central longitudinal axis and the second central longitudinal axis ranges from including 0° to less than 180°. In some preferred embodiments, for each of the two or more gas reactor elements, the opening located at the downstream end of the first reaction chamber has an annular configuration with a radius 'R'. In some embodiments of the invention, the distance between any two adjacent gas reactor elements, ranges from 0.5 R to 5 R, wherein 'R' is a radius of a circle, with the plane of the circle being oriented perpendicular to the first central axis, and the circle having a maximum radius that can be inscribed within the opening located at the downstream end of the first reaction chamber.

In some embodiments of the invention, the chemical reactor further comprises a gas converging section located downstream to the second reaction chamber having (i) a downstream end in fluid communication with one or more product outlets, and (ii) an upstream end in fluid communication with the downstream end of the second reaction chamber, and (iii) a central axis substantially co-axial to the second central longitudinal axis, wherein the gas converging section is defined by a wall surrounding the central axis, wherein the wall of the gas converging section, is joined perimetrically with the second reactor wall at the downstream end of the second reaction chamber.

In some preferred embodiments of the invention, the angle formed between the first central longitudinal axis and the second central longitudinal axis is zero. In some embodiments of the invention, the angle formed between the first central longitudinal axis and the second central longitudinal axis ranges from 0° to 90°. In some embodiments of the invention, the value of 'It' ranges from 0.05 meter to 20 meters. In some embodiments of the invention, the chemical reactor comprises at least 3 gas reactor elements and at most 200 gas reactor elements.

In some embodiments of the invention, the feed assembly unit comprises: (a) a downstream feed assembly wall, operably connected with the first reactor wall, wherein the downstream feed assembly wall surrounds the first central longitudinal axis; (b) an upstream feed assembly wall that is axially spaced upstream from the downstream feed assembly wall and surrounds the first central longitudinal axis; wherein the downstream feed assembly wall and the upstream feed assembly wall together defines in part, the mixing chamber for mixing two or more feed streams, wherein the mixing chamber is operably connected to the upstream end of the first reaction chamber; and (c) two or more feed inlet flow spaces, each in fluid communication with the mixing chamber, and each configured to inject a feed stream into the mixing chamber at radial and/or non-radial direction with regard to the first central longitudinal axis.

In some embodiments of the invention, the bottom plate has two or more plate openings, each coupled to the opening of a first reaction chamber of a gas reactor element, so that two or more second reaction chamber inlets are positioned at the bottom plate. In some embodiments of the invention, the second reactor wall has two or more wall openings, each coupled to the opening of a first reaction chamber of a gas reactor element so that two or more second reaction chamber inlets are positioned at the second reactor wall. In some embodiments of the invention, at least one second reaction chamber inlet is positioned at the second reactor wall and at least one second reaction chamber inlet is positioned at the bottom plate.

In some embodiments of the invention, the first reactor wall circumferentially surrounds the first central longitudinal axis, the second reactor wall circumferentially surrounds the second central longitudinal axis, and the bottom plate is perpendicular to the second central longitudinal axis.

In some embodiments of the invention, each feed inlet flow space is provided with a circumferentially spaced apart guide vanes, oriented to facilitate a feed stream to flow radially in a spiraling fluid flow pattern, with regard to the first central longitudinal axis. In some embodiments of the invention, each feed inlet flow space is coupled to a manifold configured to inject a feed stream tangentially into the feed inlet flow space.

In some embodiments of the invention, each gas reactor element further comprises a reactor inlet assembly located between the first reaction chamber and the feed assembly unit, wherein the reactor inlet assembly comprises a conduit defined by a circumferential wall surrounding the first central longitudinal axis and extending from an upstream end to an opposite downstream end of the conduit, wherein, i) the downstream end of the conduit is in fluid communication with the upstream end of the first reaction chamber, and ii) the upstream end of the conduit is in fluid communication with the mixing chamber, further wherein, the downstream feed assembly wall joins the circumferential wall of the conduit at the upstream end of the conduit and the first reactor wall perimetrically joins the circumferential wall of the conduit at the downstream end of the conduit. In some embodiments of the invention, the conduit of the reactor inlet assembly has a circumferential wall of tapering width extending from the downstream end and the upstream end of the conduit, to an annular constricted neck portion, located between the downstream end and the upstream end of the conduit.

In some embodiments of the invention, the invention is directed to a method of producing chemical products using the chemical reactor of claim 1, wherein the method comprises: (a) introducing two or more feed streams independently in at least two feed inlet flow spaces located in each of the two or more gas reactor elements; (b) mixing the two or more feed streams in the mixing chamber of each gas reactor element and forming a swirling gas mixture; (c) combusting a portion of the swirling gas mixture and forming a first product stream comprising a mixture of a combustion product stream and a portion of the swirling gas mixture that is not combusted; (d) introducing a portion of the first product stream into the first reaction chamber; (e) subjecting the first product stream present in the first reaction chamber to a first reaction condition and forming a second product stream; (f) introducing a portion of the second product stream through a second reaction chamber inlet into the second reaction chamber; (g) subjecting two or more second product streams obtained independently from each gas reactor element, to a second reaction condition and forming a third product stream; and (h) removing a portion of the third product stream through one or more product outlets and obtaining the chemical products.

In some embodiments of the invention, two or more feed streams comprises at least one hydrocarbon feed and at least one non-hydrocarbon feed. In some embodiments of the invention, the first reaction condition and the second reaction condition is a reaction condition suitable for cracking. In some embodiments of the invention, the first reaction condition and the second reaction condition is a reaction condition suitable for pyrolysis. In some embodiments of the invention, the hydrocarbon feed stream is selected from methane, naphtha, LPG, liquid feed, solid plastic particles, vaporized hydrocarbons having two to thirty carbon atoms, and mixtures thereof. In some embodiments of the invention, the non-hydrocarbon feed stream, is selected from oxygen, hydrogen, steam, carbon dioxide, carbon monoxide, and mixtures thereof.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

FIG. 8 particularly illustrates swirling flow rotational directions can be the same for all gas reactor elements or have different flow directions in order to minimize the flow interferences between the gas reactor elements.

DETAILED DESCRIPTION

Figure 1:
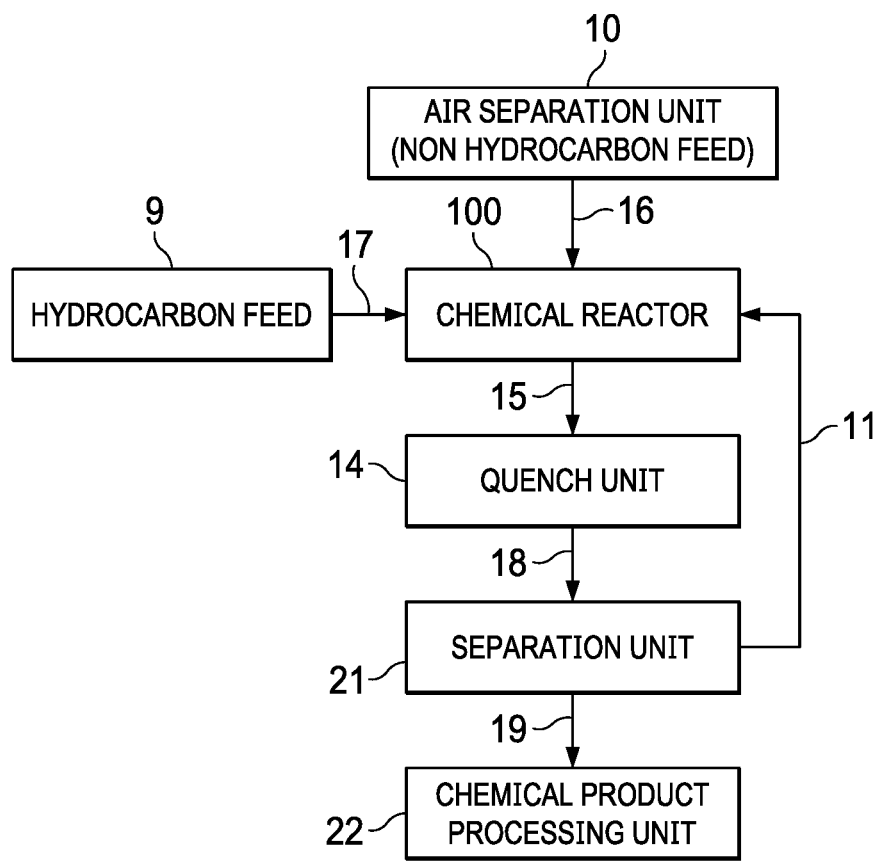
FIG. 1 is a process flow diagram for the conversion of hydrocarbon feed stream to high value chemicals using a chemical reactor designed in accordance with an embodiment of the invention and coupled to a quencher and air separation unit.

The invention is based, in part, on a chemical reactor having a unique arrangement of reaction chambers, suitable for the conversion of hydrocarbon feed to commercially high value chemical products at high productivity and improved process efficiency. Advantageously, the invention enables a skilled artisan to scale up production of commercially high value chemicals by synergistically assembling two or more of the reactor elements into a single reactor system.

The following includes definitions of various terms and phrases used throughout this specification.

The terms "wt. %", "vol. %" or "mol. %" refers to a weight, volume, or molar percentage of a component, respectively, based on the total weight, the total volume, or the total moles of the material that includes the component. In a non-limiting example, 10 moles of a component in 100 moles of the material means 10 mol. % of the component. The term "M" refers to a molar concentration of a component, based on the moles per 1 L volume. The term "mM" means one thousandth of an "M". Any numerical range used through this disclosure shall include all values and ranges there between unless specified otherwise. For example, a boiling point range of 50° C. to 100° C. includes all temperatures and ranges between 50° C. and 100° C. including the temperature of 50° C. and 100° C.

The use of the words "a" or "an" when used in conjunction with the term "comprising," "including," "containing," or "having" in the claims or the specification may mean "one," but it is also consistent with the meaning of "one or more," "at least one," and "one or more than one." The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. The process of the present invention can "comprise", "consist essentially of," or "consist of" particular ingredients, components, compositions, etc., disclosed throughout the disclosure.

As used herein, the expressions "upstream" and "downstream" as used throughout this disclosure with respect to describing various components of the inventive chemical reactor (100), shall refer to the position of a reactor section or a component with respect to the direction of overall fluid flow. For example, the expression "upstream section of a reaction chamber" means the part of the reaction chamber in which a gaseous stream is introduced or the part of the reaction chamber in which a gaseous stream first flows into the reaction chamber. Accordingly, the expression "downstream section of a reaction chamber" means the section of the reaction chamber from which a gaseous stream exists or flows out.

The expression "operably connected" as used throughout this disclosure, means any two reactor element features or elements are connected either directly or indirectly and the flow of gaseous or fluid stream takes place from one element to the other directly or indirectly. For example, if element 'A' and element 'B' are operably connected, then a gaseous or fluid stream will flow from 'A' to 'B' directly or the gaseous stream will flow indirectly through another element 'C', positioned between 'A' and 'B'.

Figure 2:
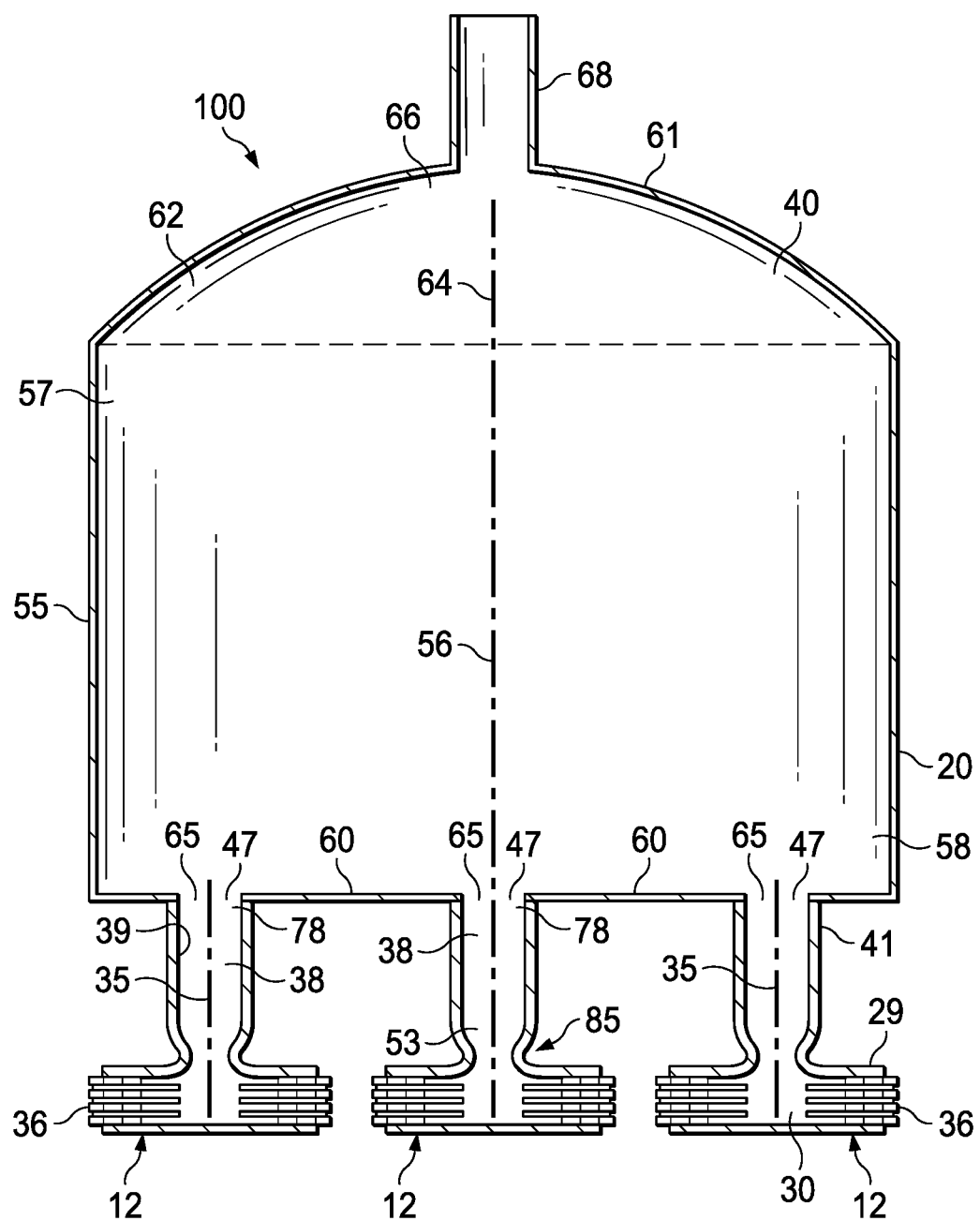
FIG. 2 is a cross-sectional view of a chemical reactor designed in accordance with an embodiment of the invention having three gas reactor elements coupled to the second reaction chamber, with the angle formed between the first central longitudinal axis and the second central longitudinal axis being 0°.

The present invention relates to a chemical reactor having two or more gas reactor elements coupled to a common reactor system, which is configured to receive product streams generated from each of the gas reactor elements. In some embodiments of the invention, each of the two or more gas reactor elements, have identical features, components and configuration. Referring to FIG. 2, in some embodiments of the invention, the invention relates to a chemical reactor (100) comprising: (a) two or more gas reactor elements (12), (b) a second reaction chamber (20), which can be regarded as the common reactor system, coupled with each of the two or more gas reactor elements (12) and configured to independently receive a product stream from each of the two or more gas reactor elements (12); and (c) a gas converging section (40) located downstream to the second reaction chamber (20).

In some aspects of the invention, the chemical reactor (100) comprises at least 3 gas reactor elements and at most 200 gas reactor elements, alternatively at least 4 gas reactor elements and at most 100 gas reactor elements, alternatively at least 10 gas reactor elements and at most 20 gas reactor elements. In some preferred embodiments of the invention, the number of gas reactor elements (12) present in the chemical reactor (100) is seven. In some embodiments of the invention, each of the gas reactor elements (12) may have a similar configuration and similar components to those reactors described and shown in U.S. Pat. No. 11,020,719 and in International Publication No. WO2020/086681A2, each of which are incorporated herein by reference in their entireties for all purposes, including the description and discussion of the reactor configurations and their various components.

Figure 5:
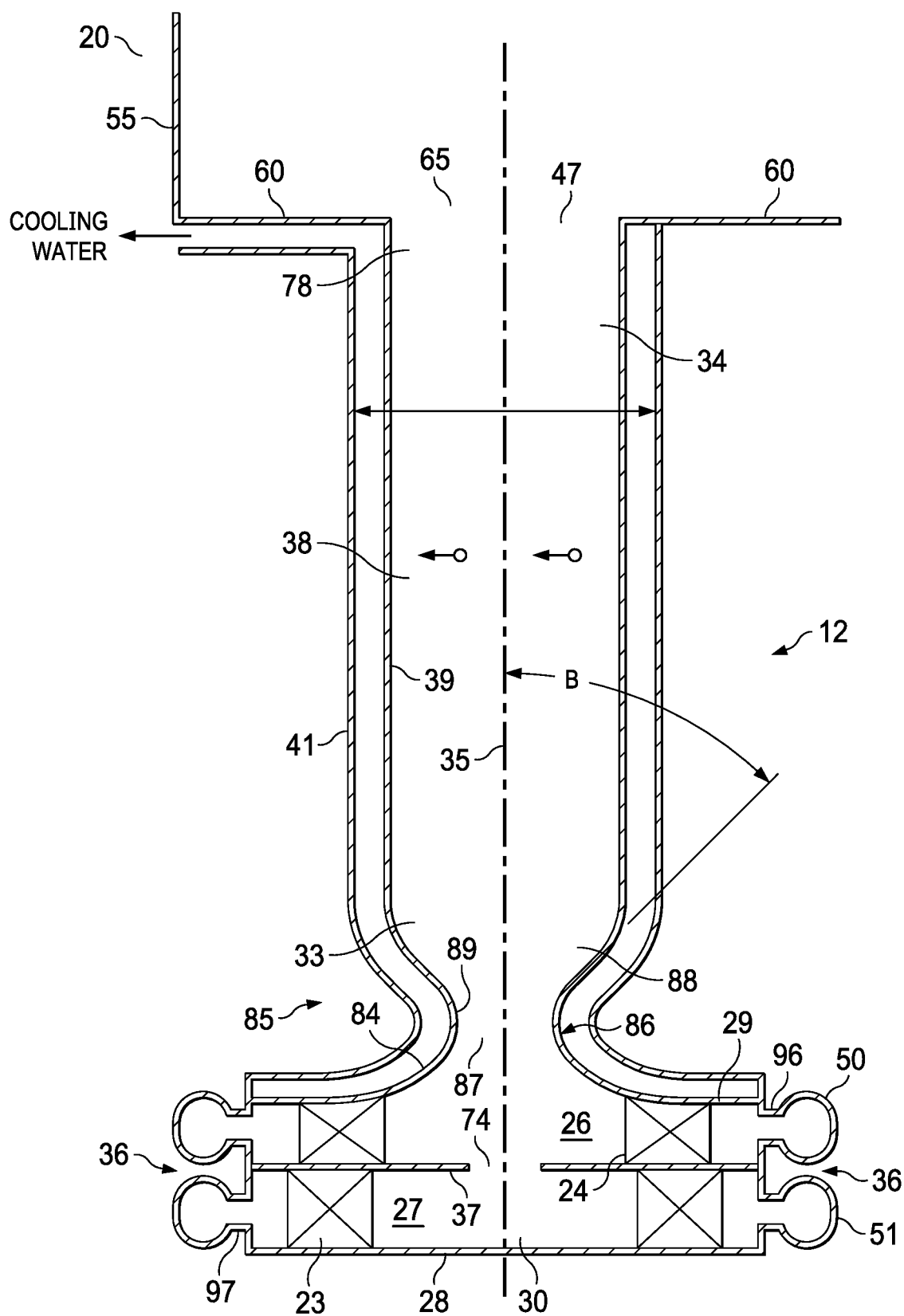
FIG. 5 is a cross-sectional view of a gas reactor element, which is coupled to a second reaction chamber and having two radial feed inlet flow spaces defined by a single gas partition wall.

Referring to FIG. 5, in some embodiments of the invention, each of the gas reactor elements (12) comprises a first reaction chamber (38) having (1) an upstream end (33), and (2) a downstream end (34), wherein the first reaction chamber (38) is defined by a first reactor wall (39) surrounding a first central longitudinal axis (35). In some embodiments of the invention, the first reactor wall (39) circumferentially surrounds the first central longitudinal axis (35) so that the first reactor wall (39) has a cylindrical configuration. In some embodiments of the invention, first reactor wall (39) can have any of cylindrical, square, elliptical, triangular, rectangular configuration or any other shape or configuration, without affecting the flow of the product stream from the first reaction chamber.

Figure 9:
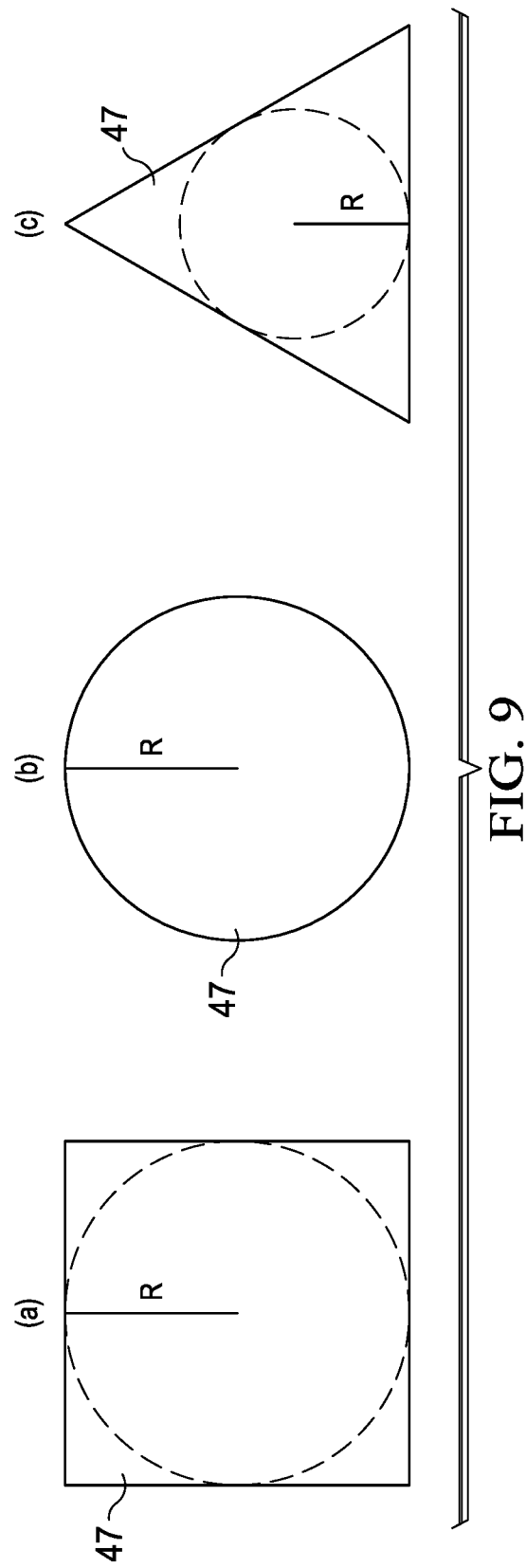
FIG. 9 illustrates as various embodiments of the invention, an overhead (top) cross-sectional view of the opening located at the downstream end of the first reaction chamber, having a circle of radius 'It' inscribed in the opening. Part (a) of FIG. 9 denotes a square configuration, part (b) of FIG. 9 denotes an annular (circular) configuration of the opening, and part (c) denotes a triangular configuration of the opening.

In some embodiments of the invention, the first reaction chamber has an opening located at the downstream end of the first reaction chamber. The opening can have any suitable shape such as annular, square, elliptical, triangular, rectangular, or any other shape or configuration without affecting the flow of the product stream from the first reaction chamber. Referring to FIG. 5, in some preferred embodiments of the invention, the first reaction chamber (38) has an opening (47) located at the downstream end (34) of the first reaction chamber (38). A convenient way of expressing the dimension of the opening (47) is by defining a radius 'R' of the largest circle (having maximum radius) that can be inscribed within the opening (47). In other words, 'R' is a radius of a circle, with the plane of the circle being oriented perpendicular to the first central axis (35), and the circle having a maximum radius that can be inscribed within the opening located at the downstream end of the first reaction chamber. The expression "inscribed" as used herein means the circle with the largest area that can be fitted within the opening (47). FIG. 9 provides an illustration of the largest circle with radius 'R' which can be inscribed within the opening (47) having various shapes and configurations. Accordingly, in some embodiments of the invention, the opening has a square configuration (FIG. 9 part (a)) such that the length of each side of the square is 2 R. Similarly, if the opening (47) is circular or annular configuration (FIG. 9 part (b)), the largest circle that can be inscribed in the opening (47) will have its radius equal to the radius of the opening (47). In some aspects of the invention, the value of 'R' ranges from 0.05 meter to 20 meters, alternatively from 0.1 meter to 15 meters, or alternatively from 1 meter to 10 meters.

In some embodiments of the invention, the opening (47) located at the downstream end (34) of the first reaction chamber (38) has an annular configuration with a radius 'R'. In some embodiments of the invention, the first reactor wall (39) has a cylindrical configuration, the opening (47) has an annular configuration and the radial distance between the first central longitudinal axis (35) and the first reactor wall (39) is 'R'.

In some embodiments of the present invention, the first reaction chamber (38) has a length ranging from 1 R to 10 R, alternatively from 2 R to 6 R, or alternatively from 4 R to 8 R, wherein 'R' is a radius of a circle, with the plane of the circle being oriented perpendicular to the first central axis (35), and the circle having a maximum radius that can be inscribed within the opening (47) located at the downstream end (34) of the first reaction chamber (38). In some aspects of the invention, the first reaction chamber (38) has a length ranging from 0.05 meter to 200 meters, alternatively from 0.2 meter to 90 meters, or alternatively from 4 meters to 80 meters.

Referring to FIG. 2, the expression "length of the first reaction chamber" as used though out this disclosure means the perpendicular length between inlet (53) of the first reaction chamber (38) located at the upstream end of the first reaction chamber (38) and the opening (47) located at the downstream end of the first reaction chamber (38). For the purposes of the measurement of the length of the first reaction chamber (38), a transverse planar cross section (perpendicular to the first central longitudinal axis) extending across the inlet (53) and a transverse planar cross section (perpendicular to the first central longitudinal axis) extending across the opening (47) are considered as the end points of the perpendicular length between the opening (47) and the inlet (53).

Referring to FIG. 5, in some embodiments of the invention, each of the two or more gas reactor elements (12) have identical features, components and configuration including the opening (47) of the first reaction chamber (38). In some preferred embodiments of the invention, for each of the two or more gas reactor elements (12), the opening (47), has an annular configuration and each having a radius of 'R'. In some aspects of the invention, the distance between any two adjacent gas reactor elements ranges from 0.5 R to 5 R, alternatively from 0.8 R to 3 R, alternatively from 1 R to 2 R, wherein 'R' is a radius of a circle, with the plane of the circle being oriented perpendicular to the first central longitudinal axis (35), and the circle having a maximum radius that can be inscribed within the opening (47) located at the downstream end (34) of the first reaction chamber (38). The distance between the gas reactor elements is measured by the radial distance between the first reactor walls of any two adjacent gas reactor elements.

Figure 8:
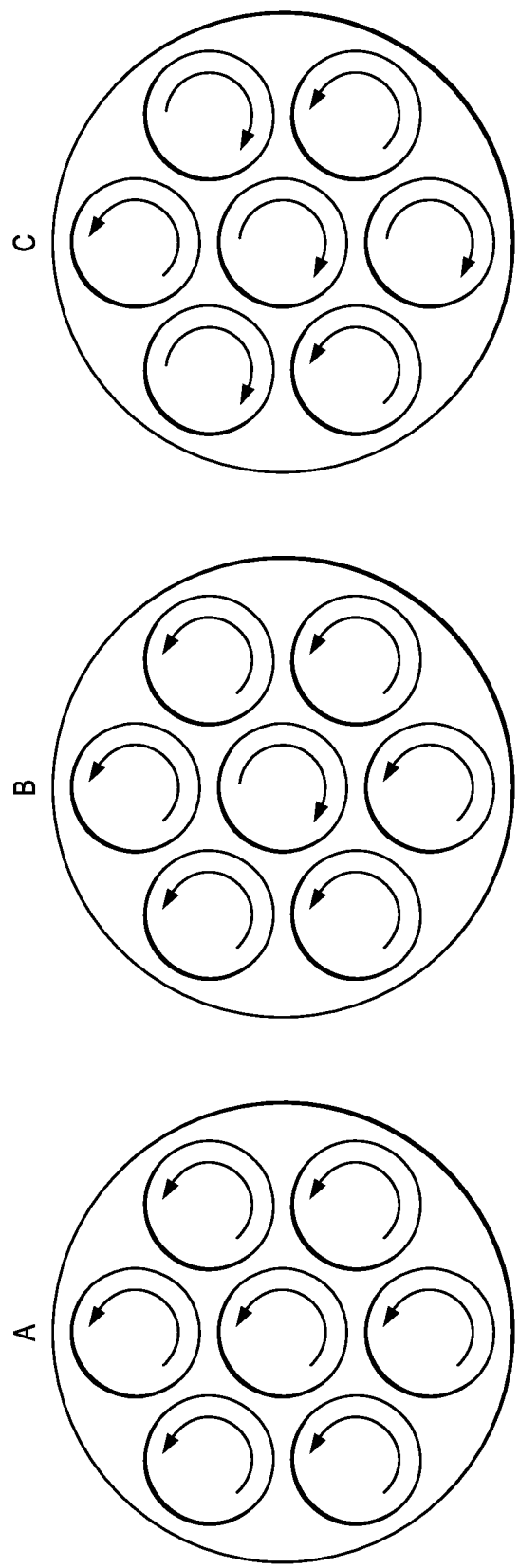
FIG. 8 illustrates as an embodiment of the present invention, an overhead (top) cross-sectional view of swirling product stream from 7 different gas reactor elements, each of which are connected to the second reaction chamber.

As illustrated under FIG. 8 an overhead (top) cross-sectional view of swirling product stream from 7 different gas reactor elements, each of which are connected to the second reaction chamber at the bottom. FIG. 8 particularly illustrates swirling flow rotational directions, which can be the same for all gas reactor elements, or have different flow directions in order to minimize the flow interferences between the gas reactor elements. In some aspects of the invention, the distance between any two adjacent gas reactor elements ranges from 0.025 meter to 100 meters, alternatively from 0.08 meter to 45 meters, or alternatively from 1 meter to 20 meters. Without wishing to be bound by any specific theory, it is believed that by ensuring a suitable distance between adjacent gas reactor elements, chances of adverse flow dynamics of product streams flowing into the second reaction chamber is mitigated thereby enabling suitable operating efficiency of the inventive chemical reactor (100).

Referring to FIG. 5, in some embodiments of the invention, the feed assembly unit (36) of each gas reactor element (12) comprises: (a) a downstream feed assembly wall (29), operably connected with the first reactor wall (39), wherein the downstream feed assembly wall (29) surrounds the first central longitudinal axis (35); (b) an upstream feed assembly wall (28) that is axially spaced upstream from the downstream feed assembly wall (29) and surrounds the first central longitudinal axis (35); wherein the downstream feed assembly wall (29) and the upstream feed assembly wall (28) together defines in part, the mixing chamber (30) for mixing two or more feed streams, wherein the mixing chamber (30) is operably connected to the upstream end (33) of the first reaction chamber (38); and (c) two or more feed inlet flow spaces, each in fluid communication with the mixing chamber (30), and configured to inject a feed stream into the mixing chamber (30) at radial and/or non-radial direction with regard to the first central longitudinal axis (35). In some embodiments, the feed injection may be tangential with respect to the first central longitudinal axis (35) so that the feed is introduced in an inwardly swirling flow pattern. In some aspects of the invention, the downstream feed assembly wall (29) and the upstream feed assembly wall (28) are oriented perpendicular to the first central longitudinal axis (35). The expression "configured to inject a feed stream into the mixing chamber at radial direction" means the feed is injected at a direction pointing perpendicular or substantially perpendicular (maximum deviation of 200) to the first central longitudinal axis (35). The expression "non-radial" as used herein means the feed is injected at any direction other than radial direction with regard to the first central axis.

In some preferred embodiments of the invention, the feed assembly unit (36) comprises two feed inlet flow spaces. Referring to FIG. 5, in some preferred embodiments of the invention, the feed assembly unit (36), comprises two feed inlet flow spaces, a first feed inlet flow space (27) and a second feed inlet flow space (26), each configured to inject a feed stream in the mixing chamber (30) at a radial direction, with regard to the first central longitudinal axis (35), wherein each of the radial feed inlet flow space is defined by a gas partition wall (37) having a central opening (74) surrounding the first central longitudinal axis (35). In some embodiments of the invention, the gas partition wall (37) is orientated perpendicular to the first central longitudinal axis (35). The first feed inlet flow space (27) is defined by the upstream feed assembly wall (28) and the gas partition wall (37). The second feed inlet flow space (26) is defined by the downstream feed assembly wall (29) and the gas partition wall (37).

Figure 7:
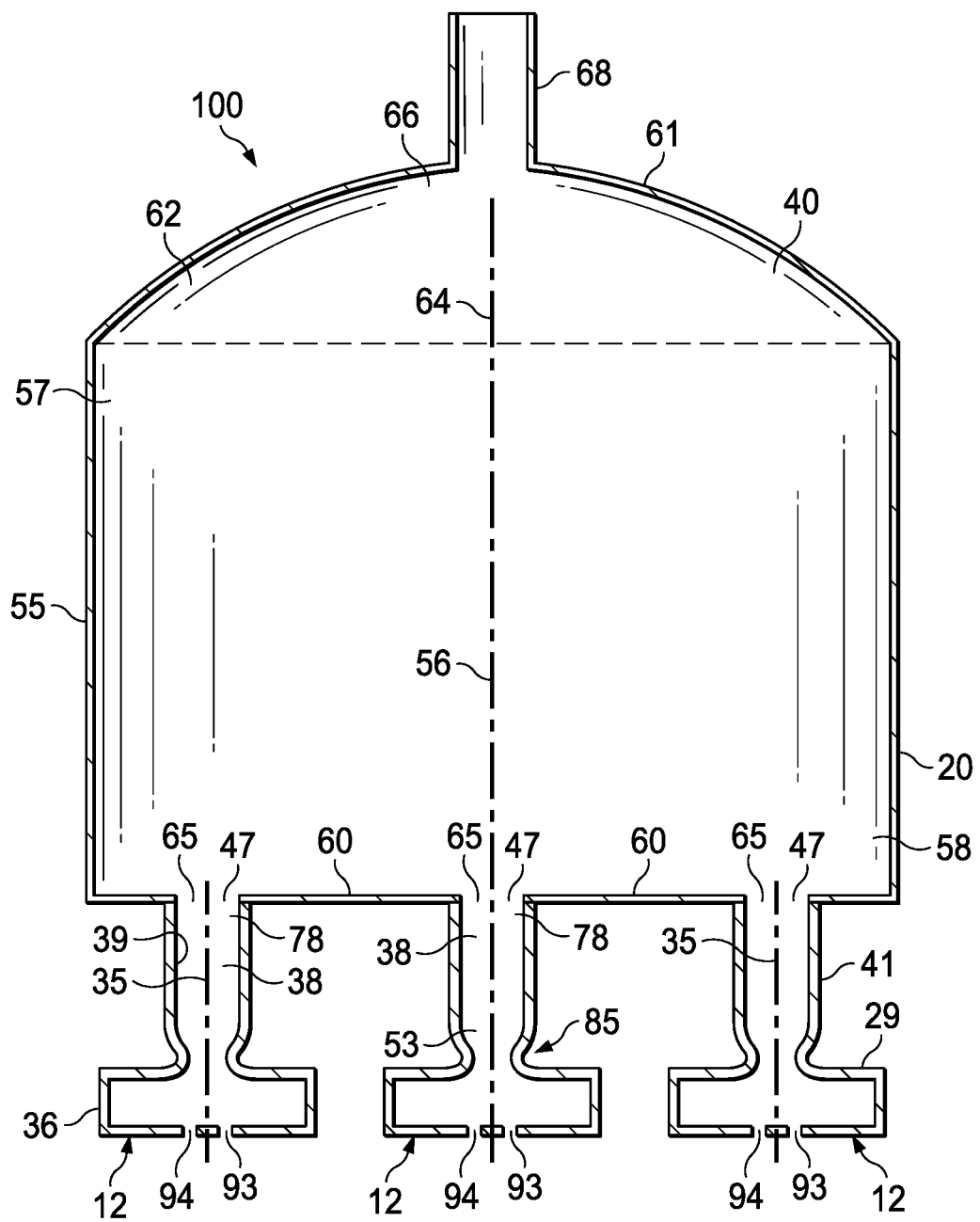
FIG. 7 is a cross-sectional view of a chemical reactor designed in accordance with an embodiment of the invention, having three gas reactor elements coupled to the second reaction chamber and each of the gas reactor elements have two co-axial feed inlet flow spaces.

Referring to FIG. 7, in some embodiments of the invention, the feed assembly unit (36), comprises one or more co-axial feed inlet flow space (93) and (94). In this instance, two co-axial inlet flow spaces (93) and (94) are shown. Each is configured to inject one or more feed stream into the mixing chamber at an axial direction with regard to the first central longitudinal axis. In some embodiments of the invention, each of the axial feed inlet flow space (93) and (94) is coupled to an opening located at the upstream feed assembly wall so that the axial feed inlet flow spaces (93) and (94) are parallel to the first central longitudinal axis (35). The expression "axial feed inlet flow space" as used herein means that feed is injected into the feed assembly unit (36) in a direction parallel or substantially parallel (deviation of at most 20° to the central axis) to the first central longitudinal axis (35).

In some embodiments of the invention, each feed inlet flow space is provided with a circumferentially spaced apart guide vanes, with each of such guide vanes being oriented to facilitate a feed stream to flow radially in a spiraling fluid flow pattern, with regard to the first central longitudinal axis. In some embodiments of the invention, each feed inlet flow space is coupled to a manifold configured to inject a feed stream into the feed inlet flow space. In some aspects of the invention, the manifold is configured to inject a feed stream tangentially into the feed inlet flow space. In some aspects of the invention, each manifold comprises a gas inlet located at the outer periphery of the feed inlet flow space.

Referring to FIG. 5, in some embodiments of the invention, the first feed inlet flow space (27) and the second feed inlet flow space (26) are provided with circumferentially spaced apart guide vanes (23) and (24), oriented to facilitate a feed stream to flow radially in a spiraling fluid flow pattern, with regard to the first central longitudinal axis (35). In some embodiments of the invention, each of the feed inlet flow space (26) and (27) may be referred to as radial feed inlet flow space. In some embodiments of the invention, the first feed inlet flow space (27), the second feed inlet flow space (26) are each coupled to a manifold (50) and (51) respectively and configured to inject a feed stream into the respective feed inlet flow space. In some embodiments of the invention, the manifold (50) and (51) are each coupled to a feed source comprising either a hydrocarbon feed source or a non-hydrocarbon feed source.

In some aspect of the invention, the operation of the manifolds (50) and (51), and the orientation of the guide vanes (23) and (24) can be practiced by a skilled person as described in U.S. Pat. No. 11,020,719. For example, in some aspects of the invention, the feed stream from the manifolds (50) and (51), are delivered tangentially to the flow spaces (26) and (27) where the guide vanes (23) and (24) further facilitate in directing the feed stream to flow in an inwardly swirling or spiraling fluid flow pattern within the flow spaces (26) and (27). In some aspects of the invention, gas inlets (96), (97) from the manifolds (50) and (51), respectively, may be directed tangentially into the flow spaces (26), (27) so that the gas feeds are not only directed radially toward the first central longitudinal axis (35) from the inlets (96) and (97) but also directed tangentially around the first central longitudinal axis (35) to provide an inwardly swirling flow pattern. In some aspects of the invention, the gas inlets (96), (97) from the manifolds (50) and (51), are each connected to a feed source which supplies the feed to the inlets.

In some aspects of the invention, each of the guide vanes (23) and (24) may be a planar member that is oriented in a plane that is parallel to the first central longitudinal axis (35) and extends between the walls (28), (29), and (37). In some aspects of the invention, the guide vanes (23) and (24) are circumferentially spaced at an equal distance from one another. In some embodiments of the invention, the guide vanes (23) and (24) are fixed in place, with the upper and lower side edges of the guide vanes (23) and (24) being joined along their lengths or a portion of their lengths, to the walls (28), (29), and (37) so that there are no air gaps between the side edges of the vanes (23) and (24) and the walls (28), (29), and (37).

In some embodiments of the invention, the guide vanes (23) and (24) are movable so that the upper and lower side edges of the guide vanes (23) and (24) are closely spaced from the walls (28), (29), and (37) to provide a small clearance for such movement while retaining minimum air gaps for the feed gases to pass through. In some embodiments of the invention, the guide vanes (23) and (24) are oriented so that the plane of the guide vane is in a non-parallel or slanted orientation relative to the first central longitudinal axis (35). In such cases, the side edges of the guide vanes (23) and (24) are fixed to the walls (28), (29), and (37) or remain closely spaced from walls (28), (29), and (37) to minimize air gaps for the feed to pass through. In some embodiments of the invention, each of the guide vanes (23) and (24) are configured as airfoils having curved surfaces, and oriented with the width being parallel or non-parallel to the first central longitudinal axis (35), to provide desired flow characteristics. The guide vanes (23) and (24) of each flow space (26) and (27) may be mounted on actuators (not shown) so that they can be selectively movable to various positions to provide a selected inwardly spiraling flow pattern. The guide vanes (23) and (24) may be pivotal about an axis that is parallel to the first central longitudinal axis (35) so that the vanes (23) and (24) may be moved to various positions.

In some aspects of the invention, the orientation of the guide vanes (23) and (24) as well as the orientation of the tangential gas inlets (96) and (97), are configured to ensure the gas feed stream to flow in a swirling flow in the feed inlet space (26) and (27). In some embodiments of the invention, each of the guide vanes (23) and (24) may be oriented at a specific angle referred to as Angle A, which is the angle formed between the line extending radially from the first central longitudinal axis (35) and the tangential line representing the orientation of each of the guide vanes (23) and (24). Such angle is shown in International Publication No. WO2020/086681A2. In some embodiments of the invention, the angle A may range from 50° to 85°, alternatively from 60° to 75°. In some aspects of the invention, the guide vanes (23) and (24) may be permanently oriented at an angle A within this range.

As shown in FIG. 2, in some preferred embodiments of the invention, the feed assembly unit (36) comprises three gas partition walls, as described in International Publication No. WO2020/086681A2, positioned axially between the upstream feed assembly wall and the downstream feed assembly wall and each gas partition wall having a central opening and each gas partition wall being oriented perpendicular to the first central longitudinal axis (35). In some aspects of the invention, the three gas partition walls together with the feed assembly walls, define four feed inlet space configured to inject at least one hydrocarbon feed, at least one non-hydrocarbon feed and at least one hydrogen-rich fuel stream and steam, into the feed assembly unit (36).

Referring to FIG. 5, as an embodiment of the present invention, each gas reactor element (12) further comprises a reactor inlet assembly (85) located between the first reaction chamber (38) and the feed assembly unit (36), wherein the reactor inlet assembly (85) comprises a conduit (86) defined by a circumferential wall (84) surrounding the first central longitudinal axis (35) and extending from an upstream end (87) to an opposite downstream end (88) of the conduit (86), wherein, i) the downstream end (88) of the conduit (86) is in fluid communication with the upstream end (33) of the first reaction chamber (38), and ii) the upstream end (87) of the conduit (86) is in fluid communication with the mixing chamber (30), and further wherein, the downstream feed assembly wall (29) joins the circumferential wall (84) of the conduit (86) at the upstream end (87) of the conduit (86) and the first reactor wall (39) is joined perimetrically with the circumferential wall (84) at the downstream end (88) of the conduit (86).

In some embodiments of the invention, the conduit (86) of the reactor inlet assembly (85) has a circumferential wall (84) of tapering width extending from the downstream end (88) and the upstream end (87) of the conduit (86), to an annular constricted neck portion (89), located between the downstream end (88) and the upstream end (87) of the conduit (86). In one aspect of the invention, the conduit (86) may be in the form of a venturi, designed to enhance the flow rate of a fluid mixture flowing from the feed assembly unit (36) to the first reaction chamber (38).

In some embodiments of the invention, the conduit of the reactor inlet assembly has a circumferential wall of increasing width (not shown) extending from the upstream end of the conduit to the downstream end of the conduit so that the conduit has a divergent shape and configuration. The downstream portion of the conduit (86) forms a diverging conduit. This diverging conduit, as well as the other diverging conduits described herein, is configured for non-supersonic fluid flow. Conduits or nozzles configured for supersonic flow, such as de Laval nozzles, are configured differently from the conduit (86) to provide supersonic flow downstream to form a shockwave. The diverging conduit (86) does not form such supersonic flow or shockwave. Instead, the conduit (86) has a geometry that facilitates a recirculation and backflow of gases within the interior reaction chamber (38) near the central longitudinal axis (35) in combination with annular swirling jet gas flow adjacent to the inner reactor wall (39). As such, the diverging conduit (86) will have a greater angle of divergence than the angle of divergence typically utilized in de Laval nozzles (e.g., 15° or less). In, certain embodiments, the overall angle of divergence "B" (FIG. 5) relative to the axis (35) may be from 25° or more. In particular instances, the angle of divergence B for the diverging conduits discussed herein is from 25° to 55°. In some embodiments, the angle of divergence B is of from at least, equal to, and/or between any two of 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, and 55°. The large divergence angle does not lead to recirculation of the flow at the walls as in this unique design the upstream swirling flow is coupled with the convergent divergent nozzle.

Referring back to FIG. 5, in some aspects of the invention, the first reactor wall (39) is circumferentially surrounded along all or a portion of its length by an outer wall (41) wherein the outer wall (41) is positioned around and spaced from the first reactor wall (39) to form a cooling jacket wherein a cooling fluid, such as water is circulated through the jacket formed between the walls (39) and (41). In some other embodiments of the invention, the outer wall (41) may be formed from one or more layers of refractory material while the first reactor wall (39) may be formed of steel. Without wishing to be bound by any specific theory, it is believed such an arrangement assists in reducing heat loss and helps in sustaining the high operating temperatures typically used inside the first reaction chamber (38). Further, it is believed that the unique design and operation of each of the gas reactor element (12), the first reactor wall (39) is cooled internally by the high-velocity near-wall gas flow pushed by centrifugal forces against the reactor wall (39) so that in some embodiments of the invention no exterior cooling is required.

Referring back to FIG. 2, the chemical reactor (100) comprises a second reaction chamber (20) coupled with each of the two or more gas reactor elements (12) and configured to independently receive a product stream from each of the two or more gas reactor elements (12). The expression "independently receive a product stream" as used herein means that the product stream generated in each of the individual gas reactor elements (12) flows simultaneously into the second reaction chamber (20). In some embodiments of the invention, the second reaction chamber (20) has (i) a second central longitudinal axis (56), (ii) a downstream end (57), and (iii) an upstream end (58). In some aspects of the invention, the second reaction chamber (20) is configured to provide sufficient reaction conditions to further react the product stream that flows into the second reaction chamber (20) from the first reaction chamber (38) of each of the gas reactor element (12).

In some aspects of the invention, the second reaction chamber (20) is defined by: (1) a second reactor wall (55) surrounding the second central longitudinal axis (56), and extending from the upstream end (58) of the second reaction chamber (20) to the downstream end (57) of the second reaction chamber (20), (2) a bottom plate (60) extending across the second central longitudinal axis (56), and located at the upstream end (58) of the second reaction chamber (20), wherein the bottom plate (60) is joined perimetrically with the second reactor wall (55), and (3) a product outlet (68) operably connected with the downstream end (57) of the second reaction chamber (20). The expression "joined perimetrically" as used herein means that, all the side edges of the bottom plate (60) are connected with the second reactor wall (55) so that the bottom plate (60) forms the base of the chemical reactor (100).

In some aspects of the invention, the opening (47) of each of the first reaction chamber (38) forms a second reaction chamber inlet (65) located at the upstream end (58) of the second reaction chamber (20) so that the first reaction chamber (38) is in fluid communication with the second reaction chamber (20).

In some embodiments of the invention, the second reactor wall (55) circumferentially surrounds the second central longitudinal axis (56) so that the second reactor wall (55) has a cylindrical configuration. In some embodiments of the invention, the bottom plate (60) is perpendicular to the second central longitudinal axis (56). The length of the second reaction chamber (20) can be of any suitable dimensions depending on the residence time required for the feed stream. In some embodiments of the invention, length of the second reaction chamber (20) ranges from 2 R to 20 R, 'R' is a radius of a circle, with the plane of the circle being oriented perpendicular to the first central longitudinal axis (35), and the circle having a maximum radius that can be inscribed within the opening (47) located at the downstream end of the first reaction chamber (38) of each gas reactor element (12). In some embodiments of the invention, the second reactor wall (55) has a cylindrical configuration with the radius of the second reaction chamber (20) ranging from 2.25 R to 52 R. In some embodiments of the invention, the radius of the second reaction chamber (20) ranges from 0.15 meter to 1040 meters, alternatively from 0.15 meter to 50 meters, alternatively from 2 meters to 30 meters, alternatively from 5 meters to 20 meters.

In some aspects of the invention, the angle formed between the first central longitudinal axis (35) and the second central longitudinal axis (56) ranges from including 0° to less than 180°, alternatively from including 0° to 90°, alternatively from 10° to 45°. In some preferred aspects of the invention, the angle formed between the first central longitudinal axis (35) and the second central longitudinal axis (56) is 0°. As may be appreciated by a skilled person, when the angle between the first central longitudinal axis (35) and the second central longitudinal axis (56) is 0°, the gas reactor element (12) is upright and the first central longitudinal axis (35) and the second central longitudinal axis (56) are parallel to each other.

Referring to FIG. 2, in some embodiments of the invention, the bottom plate (60) has two or more plate openings (78), each coupled to the opening (47) of a first reaction chamber (38) of the corresponding gas reactor element (12) so that two or more second reaction chamber inlets (65) are positioned at the bottom plate (60). As may be appreciated by a person skilled in the art, when the second reaction chamber inlet (65) is positioned at the bottom plate (60), the product stream from the first reaction chamber (38) of a gas reactor element (12) enters the second reaction chamber (20) from the bottom of the chemical reactor (100). As illustrated in FIG. 2, as an embodiment of the present invention, the three gas reactor elements (12) are upright and the angle formed between the first central longitudinal axis (35) and the second central longitudinal axis (56) is 0°.

Figure 3:
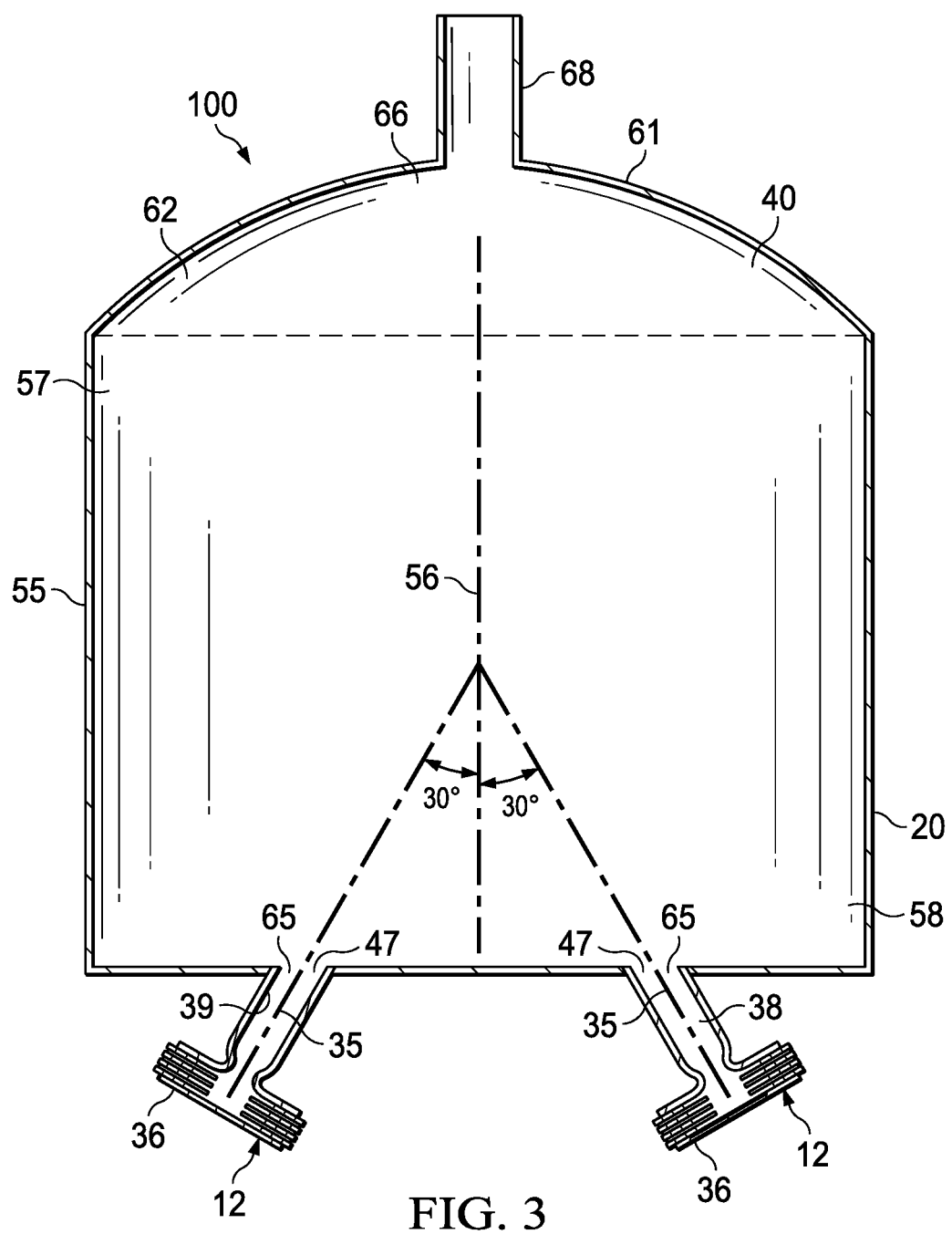
FIG. 3 is a cross-sectional view of a chemical reactor designed in accordance with an embodiment of the invention, having two gas reactor elements coupled to the second reaction chamber, with the two second reaction chamber inlets positioned at the bottom plate and the angle formed between the first central longitudinal axis and the second central longitudinal axis being 30°.

In some other embodiments of the invention, the gas reactor elements (12) are oriented at a particular angle, which may be an acute angle, with respect to the second reaction chamber (20). As illustrated by way of FIG. 3, two gas reactor elements (12) are coupled to the second reaction chamber (20) and are circumferentially spaced apart from one another about the axis 56, with two second reaction chamber inlet (65), positioned at the bottom plate (60), with the angle formed between the first central longitudinal axis (35) and the second central longitudinal axis (56) is 30°.

Figure 4:
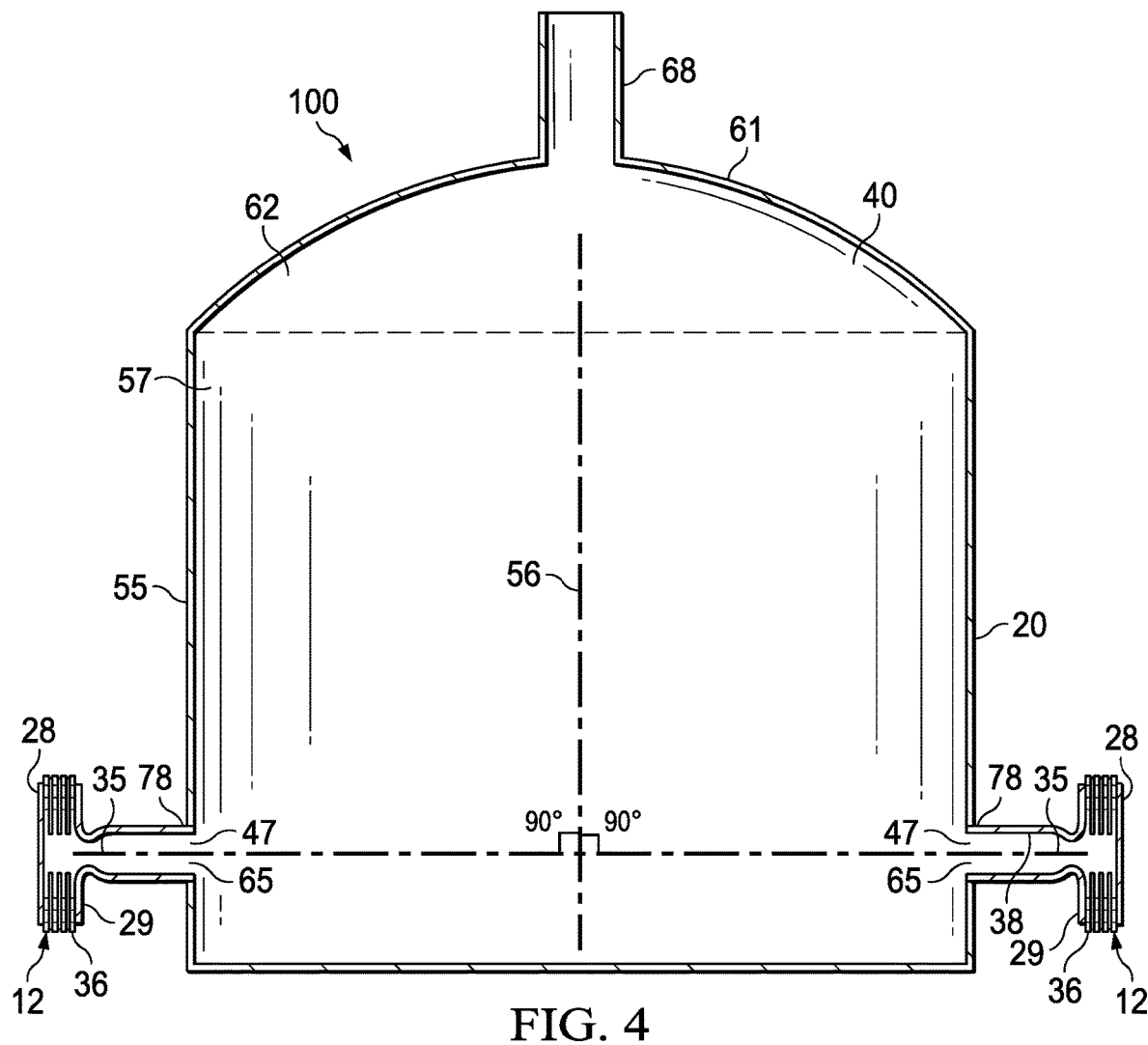
FIG. 4 is a cross-sectional view of a chemical reactor designed in accordance with an embodiment of the invention, having two gas reactor elements coupled to the second reaction chamber, with two second reaction chamber inlets positioned at the second reactor wall, with the angle formed between the first central longitudinal axis and the second central longitudinal axis being 90°.

In some aspects of the invention, the gas reactor elements are positioned at the second reactor wall so that the inlets for the second reaction chamber are positioned on the reactor walls. Referring to FIG. 4, in some aspects of the invention, the chemical reactor (100) has two or more gas reactor elements (12), each coupled to the second reaction chamber (20), with two second reaction chamber inlet (65), being positioned at the second reactor wall (55), with the angle formed between the first central longitudinal axis (35) and the second central longitudinal axis (56) being 90°. In some embodiments of the invention, the two or more reactor elements (12) may be circumferentially spaced apart along the reactor wall (55) at different positions. In many embodiments, the gas reactor elements (12) will be equally spaced apart. Thus, in the embodiment of FIG. 4, two reactor elements (12) are shown spaced apart approximately 180°. If three reactor elements were used, these may be circumferentially spaced apart a 120° and so forth. In other embodiments, the reactor elements may be non-equally circumferentially spaced apart.

Referring back to FIG. 2, in some aspects of the invention, the chemical reactor (100) comprises a gas converging section (40) located downstream to the second reaction chamber (20). In some embodiments of the invention, the gas converging section (40) has a (i) a downstream end (66) in fluid communication with a product outlet (68), and (ii) an upstream end (62) in fluid communication with the downstream end (57) of the second reaction chamber (20), and (iii) a central axis (64) substantially co-axial to the second central longitudinal axis (56). The expression "substantially co-axial" as used herein means that the second central longitudinal axis (56) is co-axial with the central axis (64) with the central axis (64) being oriented less than 10° with regard to the second central longitudinal axis (56). In some preferred aspects of the invention, the central axis (64) and the second central longitudinal axis (56) are completely co-axial with each other so that the central axis (64) and the second central longitudinal axis (56) are identical and have an angle of 0° formed between them.

In some aspects of the invention, the gas converging section (40) is defined by a wall (61) surrounding the central axis (64), wherein the wall (61) of the gas converging section (40) is joined perimetrically with the second reactor wall (55) at the downstream end (57) of the second reaction chamber (20). The expression "joined perimetrically" as used herein, means the walls of the gas converging section (40) and the second reaction chamber (20) are connected at their edges so that at least 99% by volume of the product stream from the second reaction chamber (20) passes into the gas converging section (40). In some aspects of the invention, the wall (61) of the gas converging section (40) circumferentially surrounds the second central longitudinal axis (56). In some embodiments of the invention, the wall has a tapering width extending from the upstream end (62) to converging at the downstream end (66) at the product outlet (68). The converging section 40 may be in a partial ellipsoidal or spheroidal configuration. Without being bound by any specific theory, it is believed that the gas converging section (40) allows a proper mixing and circulation of the product streams flowing from the second reaction chamber (20) with suitable residence time for mixing prior to removing the products from one or more product outlets. In some preferred embodiments, the gas converging section may be divided into two sections with each section coupled to a product outlet having a filter suitably positioned to remove harmful particulates or mitigate greenhouse emissions. In some aspects, the product outlets may be operated alternately so that the filters at the product outlet may be changed without hampering operations.

In some aspects of the invention, the invention is directed to a method of producing chemical products using the chemical reactor of the present invention, wherein the method comprises: (a) introducing two or more feed streams independently in at least two feed inlet flow spaces located in each of the two or more gas reactor elements; (b) mixing the two or more feed streams in the mixing chamber of each gas reactor element and forming a swirling gas mixture; (c) combusting a portion of the swirling gas mixture and forming a first product stream comprising a mixture of a combustion product stream and a portion of the swirling gas mixture that is not combusted; (d) introducing a portion of the first product stream into the first reaction chamber; (e) subjecting the first product stream present in the first reaction chamber, to a first reaction condition and forming a second product stream; (f) introducing a portion of the second product stream through a second reaction chamber inlet into the second reaction chamber; (g) subjecting two or more second product streams obtained independently from each gas reactor element, to a second reaction condition and forming a third product stream; and (h) removing a portion of the third product stream through one or more product outlets and obtaining the chemical products. In some embodiments of the invention, a portion of the third product stream is first introduced into the gas converging section and subsequently removed through one or more product outlets.

In some embodiments of the invention, two or more feed streams comprises at least one hydrocarbon feed and at least one non-hydrocarbon. In some embodiments of the invention, the hydrocarbon feed stream is selected from methane, naphtha, LPG, liquid feed, solid plastic particles, vaporized hydrocarbons having two to thirty carbon atoms, and mixtures thereof. In some embodiments of the invention, the non-hydrocarbon feed stream, is selected from oxygen, hydrogen, steam, carbon dioxide, carbon monoxide, and mixtures thereof. In certain embodiments of the invention, the molar ratio of hydrocarbon feed to non-hydrocarbon feed ranges from 1 to 5, more particularly from 1 to 4, and still more particularly from 1.5 to 2.5, and even still more particularly from 1.8 to 2. Such ratio may depend upon the particular operating conditions and desired products to be formed.

Referring to FIG. 5 as an embodiment of the present invention, two feed streams are introduced independently in the first feed inlet flow space (27) and the second feed inlet flow space (26) respectively of the reactor element (12). In some embodiments of the invention, the feed introduced in the feed inlet flow space (27) is oxygen gas. In some embodiments of the invention the feed introduced in the feed inlet flow space (26) is methane or hydrocarbon feed having two to ten carbon atoms. Optionally, additional feed streams comprising steam and/or hydrogen rich fuel may be introduced in the mixing chamber (30) using additional feed inlet flow spaces.

The introduction of the feed streams independently in the feed flow space instead as a mixture, mitigates risk of any unsafe operational issues. In some embodiments of the invention, the feed streams are introduced tangentially into the feed inlet flow space (27) and (26). The feed streams injected are mixed in the mixing chamber (30) to form a swirling gas mixture. In some embodiments of the invention, a portion of the swirling gas mixture may be combusted to provide necessary supply of heat for the hydrocarbon conversion process in the first reaction chamber (38). The combustion of the portion of the swirling gas mixture results in the formation of the first product stream. In some embodiments of the invention, at least a portion (at least 95% by volume) of the first product stream passes through the conduit (86) of the reactor inlet assembly (85) into the first reaction chamber (38).

The first product stream is a mixture of the products obtained from the partial combustion of the swirling gas mixture and the portion of the swirling gas mixture which is not combusted. In some embodiments of the invention, the portion of the first product stream is subjected to a first reaction condition to form a second product stream. In some embodiments of the invention, the first reaction condition is suitable for pyrolysis of the portion of the first product stream present in the first reaction chamber (38). In some embodiments of the invention, first reaction condition is suitable for cracking the first product stream present in the first reaction chamber (38).

In some embodiments of the invention, the first reaction condition is suitable for cracking or pyrolysis of a mixture of hydrocarbon feed stream and a non-hydrocarbon feed stream at a temperature condition ranging from 1000° C. to 3000° C., a pressure condition ranging from greater than 0 bar absolute pressure to 10 bar absolute pressure, and at a gas flow rate condition ranging from greater than 0 to 120 t/h. The gas flow rate value as used here is for a flow rate suitable for operating an individual gas reactor element. The heat supplied from the partial combustion of the swirling gas mixture in the mixing chamber (30) assists in imparting the first reaction condition suitable for pyrolysis or cracking of at least a portion of the first product stream.

In some embodiments of the invention, the second reaction condition is suitable for cracking or pyrolysis of a mixture of hydrocarbon feed stream and a non-hydrocarbon feed stream at a temperature condition ranging from (800° C. to 2000° C.), a pressure condition ranging from (greater than 0 bar absolute pressure to 10 bar absolute pressure), and at a flow rate condition ranging from greater than 0 to 120 'N' t/h) where 'N' is the total number of gas reactor elements coupled to the second reaction chamber (20). The gas flow rate inside the second reaction chamber is enhanced by a multiplier factor of the number of gas reactor elements which are coupled to the second reaction chamber (20).

In some embodiments of the invention, at least 95%, or alternatively at least 99% by volume of the first product stream is introduced into the first reaction chamber. In some embodiments of the invention, 100% by volume of the first product stream is introduced into the first reaction chamber. In some embodiments of the invention, at least 90%, alternatively at least 95%, or alternatively at least 99% by volume of the second product stream is introduced into the second reaction chamber. In some embodiments of the invention, 100% by volume of the second product stream is introduced into the second reaction chamber. In some embodiments of the invention, at least 90%, alternatively at least 95%, or alternatively at least 99% by volume of the third product stream is introduced into the gas converging section. In some embodiments of the invention, 100% by volume of the second product stream is introduced into the gas converging section.

In some embodiments of the present invention, the second product stream comprises hydrocarbon pyrolysis products. In some other embodiments of the invention, the second product stream comprises cracked hydrocarbon products. The gas feed streams may be introduced to provide different flow velocities to provide the Kelvin-Helmholtz instability for enhanced mixing. In some aspects of the invention, the chemical reactor is operated at a gas residence time within the first reaction chamber ranging from greater than 0 to 10 milliseconds and the gas residence time in the second reaction chamber ranging from greater than 0 to 25 milliseconds. In particular, the residence time can be tuned depending upon whether the chemical reactor is used for pyrolysis or cracking of the fee stream. For example, for pyrolysis, the total residence time in the reactor system before quenching in some instance, is less than 10 milliseconds while the total residence time in the reactor system before quenching in some instance, is less than 15 milliseconds when the feed is used for cracking.

Referring to FIG. 2, as an embodiment of the present invention, in some aspects of the invention, the second reaction chamber (20) is configured to independently receive the second product stream from each of the gas reactor elements (12) coupled to the second reaction chamber (20). In some embodiments of the invention, a portion of the second product stream is passed through a second reaction chamber inlet (65) into the second reaction chamber (20) where the portion of the second product stream is subjected to a second reaction condition to form a third product stream.

The third product stream comprises the product stream received from each of the individual gas reactor elements (12) along with additional hydrocarbon pyrolysis products or cracked hydrocarbon products produced in the second reaction chamber (20). In some embodiments of the invention, the second reaction condition and the first reaction condition are identical and are suitable for pyrolysis or cracking a portion of the second product stream present in the second reaction chamber (20). In some aspects of the invention, a portion of the third product stream passes into the gas converging section (40) and subsequently a portion of the third product stream (at least 95% by volume) or all of the third product stream is removed through the product outlet (68) to obtain the chemical products.

In some embodiments of the invention, chemical products produced in the inventive chemical reactor (100) after being removed from the product outlet (68) may be quenched and further processed and recycled, as illustrated under FIG. 1. More particularly as shown under FIG. 1, the chemical products (15) are removed from the chemical reactor (100) where the chemical products (15) may be cooled by quenching in a quenching unit (14), such as a water-droplet-spray quench vessel, or other suitable gas quench devices. The chemical products (15) typically include a mixture of cracked hydrocarbon products, hydrogen gas, steam, oxygenates, C4+ hydrocarbons, C4+ hydrocarbons, aromatics, and product olefins. The feed injected into the chemical reactor (100) originates from the air separation unit (10) and the hydrocarbon feed source (9) with the feed being introduced as two separate streams (16) and (17).

In some aspects of the invention, the quenched chemical products (18) may be delivered to a separation unit (21), where the product gases are separated to form a product stream (19) containing commercially high value products such as olefins, including ethylene, propylene, and others, and a separated gas stream (11). In some embodiments of the invention, the separated gas stream (11) typically contains hydrogen gas (H2), with minor amounts of methane (CH4), and carbon oxides of CO and CO2, which may be recycled back to the chemical reactor (100). The product stream (19) may be subjected to further processing in a processing unit (22). Accordingly, the invention enables a skilled person to design a chemical reactor suitable for scaled up production of commercially high value chemicals with excellent feed conversion and selectivity, particularly high overall C2+ yield compared to conventional crackers or pyrolysis reactors. The inventive chemical reactor of the present invention is relatively simple in configuration, which significantly reduces the capital and operating costs and allows scalable production of high value chemical products. In particular the present invention provides the following advantages: (1) novel swirling flow dynamics provides high temperature combustion gas at the core of the reactor and minimizes heat loss; (2) shorter residence time mitigating coke formation; (3) compact non-premixed flame provides a stable heat resource for pyrolysis and reducing flashback risks; (4) reactor is flexible and converts various feedstock or mixed feedstock to high valued olefins and other chemicals; (5) stratified streams between cracking feedstock and oxidant radicals ensured by high centrifugal force of the swirling gas mixture facilitates higher yield and selectivity; (6) reactor system allows the use of hydrogen-rich fuel minimizing byproduct formation by scavenging oxygen radicals to water formation; (7) process intensification by combining the exothermic and endothermic steps in a single reactor system; (8) simplicity in operation leading to reduced capital costs and lower operating expenses; (9) fast mixing between the combustion products and pyrolysis/cracking products provides control over the temperature of the mixed recirculation region (controlling the temperature of the hydrocarbon conversion zone); (10) reactor can operate under high flow rates with control over residence time; (11) flexible fuel burner enables a skilled person to combust hydrocarbons or a mixture without usual issues of flame stability or flame impingement.

Specific examples demonstrating some of the embodiments of the invention are included below. The examples are for illustrative purposes only and are not intended to limit the invention. It should be understood that the embodiments and the aspects disclosed herein are not mutually exclusive and such aspects and embodiments can be combined in any way. Those of ordinary skill in the art will readily recognize parameters that can be changed or modified to yield essentially the same results.

EXAMPLES

Example 1

Pyrolysis of Methane for Acetylene Production

Purpose: Example 1 illustrates a method of methane pyrolysis to acetylene using the inventive chemical reactor designed as an embodiment of the present invention. Particularly, the inventive reactor employed seven gas reactor elements to produce 15 kTA of C2+ hydrocarbons, specifically acetylene, with CO and H2 as co-products.

Methodology: Computational Fluid Dynamics (CFD) simulations, using commercial software available as the ANSYS FLUENT® software product, were conducted for the optimal design of a cracking reactor, as has been described herein, to verify its performance by numerical experiments. The swirling fluid flow, heat transfer, and detailed gas phase reactions were modeled in a two-dimensional axisymmetric CFD framework using Reynolds Averaged Navier-Stokes (RANS) approach using Reynolds Stress turbulence model.

Operating parameters: The hydrocarbon feed stream used for the purpose of Example 1, was methane and the non-hydrocarbon feed stream used was pure oxygen. The following reactor configuration and operating parameters were used for the model as shown in Table 1, Table 2, and Table 3 below:

TABLE 1

Reactor Configuration

| Number of gas reactor elements | Radius 'R' of the opening (47) of the first reaction chamber | Length of the first reaction chamber | Angle between the first central longitudinal axis and the second longitudinal axis | Angle A (degrees) for the orientation of guide vanes | Radius of the second reaction chamber |
|---|---|---|---|---|---|
| 7 | 0.28 m | 3R | 0° | 72 | 8 R |

TABLE 2

Reactor Feed Operating Conditions

| Hydrocarbon feed stream introduced | Non-hydrocarbon feed stream introduced | Molar Ratio of Feed Mixture (Methane/Oxygen) | Fuel mixture introduced | Steam feed introduced |
|---|---|---|---|---|
| Methane ($CH_4$) | Oxygen ($O_2$) | 2:1 | NA | NA |

TABLE 3

Process Conditions

| First Reaction Condition | |
|---|---|
| Temperature in first reaction chamber (° C.) | 2000° C.-2800° C. (Mean temperature: 2400° C.) |
| Pressure in the first reaction chamber | 1 bar absolute pressure |
| Residence time in the first reaction chamber (milliseconds) | 1-10 ms (Mean value: 5.5 milliseconds) |
| Flow rates of gas flow in the first reaction chamber | 2.3 t/h in each element |
| Second Reaction Condition | |
| Temperature in second reaction chamber (° C.) | 1500° C.-2000° C. (Mean temperature: 1750° C.) |
| Pressure in the second reaction chamber | 1 bar absolute pressure |
| Residence time in the second reaction chamber (milliseconds) | 2-20 ms |
| Flow rate of gas flow in the second reaction chamber | 16.1 t/h total |

Figure 6:
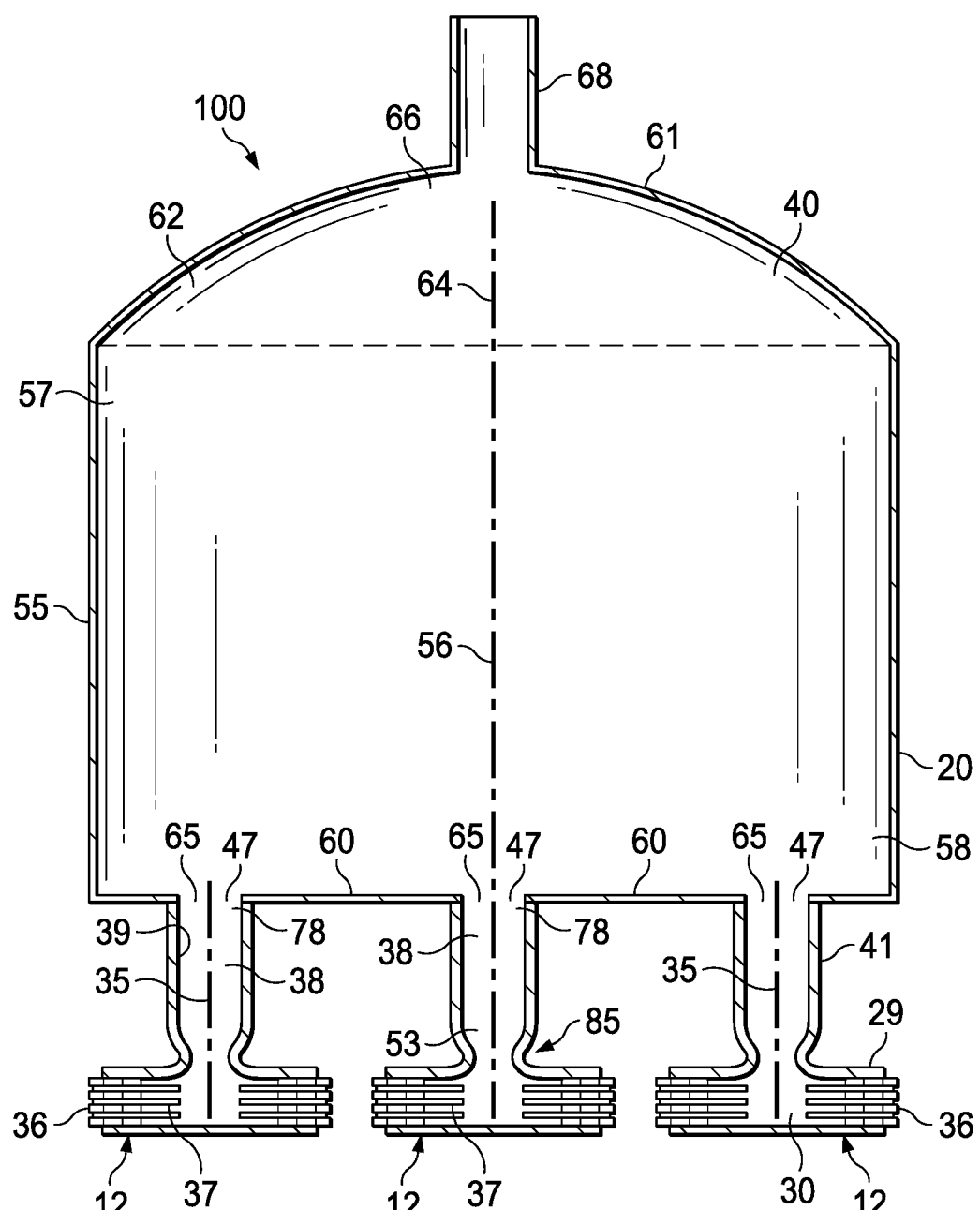
FIG. 6 is a cross-sectional view of a chemical reactor designed in accordance with Example 1 of the invention, wherein the chemical reactor has seven gas reactor elements each coupled to the second reaction chamber. For the purpose of illustration, representative three gas reactor elements have been shown in the figure.

For the purpose of Example 1 and as illustrated in FIG. 6, a simulation study was conducted for a chemical reactor (100), which involved seven different gas reactor elements (12). However, for the purpose of illustration, a representative three gas reactor elements (12) have been shown in FIG. 6. The gas reactor elements (12) were configured as shown in FIG. 5 and were oriented upright so that the first central longitudinal axis (35) and the second central longitudinal axis (56) were parallel to each other. The feed assembly unit (36) had a gas partition wall (37) and an upstream feed assembly wall (28) and a downstream feed assembly wall (29). A non-hydrocarbon feed stream of oxygen was introduced by the manifold (50) into the first feed inlet flow space (27) and a hydrocarbon feed stream of methane was introduced by the manifold (51) into the second feed inlet flow space (26). The methane and oxygen feed streams were introduced separately and mixed in the mixing chamber (30) and to form the swirling gas mixture.

Referring to FIG. 5, a portion of the swirling gas mixture was combusted to form a first product stream comprising a mixture of a combustion product stream and a portion of the swirling gas mixture that is not combusted. The first product stream was introduced into the first reaction chamber (38) through the conduit (86) of the reactor inlet assembly (85). Almost all of the first product stream (>99%) was subjected to a first reaction condition to form a second product stream. Almost all of the second product stream (>99% by volume) so obtained was introduced through the second reaction chamber inlet (65) into the second reaction chamber (20). The second product stream obtained from each of the seven gas reactor elements (12) was introduced simultaneously into the second reaction chamber (20). The mixture formed by the mix of the second product streams obtained from the seven gas reactor elements, was subjected to a second reaction condition of pyrolysis to form the third product stream. Almost all of the third product stream (>99% by volume) was introduced into the gas converging section (40) and subsequently almost all of the third product stream (>99% by volume) was passed through the product outlet (68) to obtain the chemical products comprising acetylene and other pyrolysis by-products. The overall schematic diagram of the process was practiced as shown in FIG. 1.

Comparative Example: As a comparative example, feed mixture of methane and oxygen in the proportion shown under Example 1, was introduced in a single gas reactor element, identical to that disclosed in U.S. Pat. No. 11,020,719. The feed mixture introduced in the chemical reactor was subjected to pyrolysis conditions as described for the gas reactor element in the inventive Example 1. However, for the comparative reactor system, the chemical product obtained from the individual gas reactor element was not introduced in a second reaction chamber and was instead directly removed from the gas reactor element and analyzed for product yield, selectivity measurements.

Results: The chemical products obtained from the inventive chemical reactor system and the comparative system were analyzed in details. The simulation software was configured to calculate the yield, conversion and selectivity parameters as shown below in Table 4 below.

TABLE 4

| Product Analysis | | |
| --- | --- | --- |
| | Inventive Example 1 | Comparative Example 1 A |
| $C_{2+}$ hydrocarbon yield (%) | 25% | 27% |
| Methane conversion (%) | 82% | 82% |
| $C_{2+}$ selectivity | 30.5% | 33% |

From the results shown in Table 4, the inventive chemical reactor with its unique configuration is able to provide similar methane conversion, C2+ hydrocarbon yield and selectivity compared to existing single element reactor system described in U.S. Pat. No. 11,020,719 (Comparative Example 1 A), enabling scale-up of the reactor at similar performances.

While the invention has been shown in some of its forms, it should be apparent to those skilled in the art that it is not so limited, but is susceptible to various changes and modifications without departing from the scope of the invention based on experimental data or other optimizations considering the overall economics of the process. Accordingly, it is appropriate that the appended claims be construed broadly and in a manner consistent with the scope of the invention.

What is claimed is:

1. A chemical reactor, comprising:
two or more gas reactor elements, wherein each of the gas reactor element comprises:
i. a first reaction chamber comprising an upstream end and a downstream end, wherein the first reaction chamber is defined by a first reactor wall defining the first reaction chamber and the first reaction chamber has an opening located at the downstream end of the first reaction chamber;
ii. a feed assembly unit operably connected with the first reaction chamber, wherein the feed assembly unit, comprises: 1) a mixing chamber defined by one or more feed assembly walls, wherein the mixing chamber is operably connected to the upstream end of the first reaction chamber and at least one feed assembly wall is operably connected with the first reactor wall; and 2) two or more feed inlet flow spaces, each in fluid communication with the mixing chamber and configured to inject a feed stream into the mixing chamber;
a second reaction chamber coupled with each of the two or more gas reactor elements and configured to independently receive two or more product streams from the two or more gas reactor elements, wherein the second reaction chamber comprises a downstream end and an upstream end and the second reaction chamber is defined by a second reactor wall extending from the upstream end of the second reaction chamber to the downstream end of the second reaction chamber; and wherein
the opening of each of the first reaction chamber forms a second reaction chamber inlet located at the upstream end of the second reaction chamber so that the first reaction chamber is in fluid communication with the second reaction chamber.

2. The chemical reactor of claim 1, wherein the first reaction chamber has a length ranging from 1 R to 10 R, wherein 'R' is a radius of a circle, with the plane of the circle being oriented perpendicular to the first central axis, and the circle having a maximum radius that can be inscribed within the opening located at the downstream end of the first reaction chamber.

3. The chemical reactor of claim 2, wherein the value of 'R' ranges from 0.05 meter to 20 meters.

4. The chemical reactor of claim 1, wherein the chemical reactor further comprises a gas converging section located downstream to the second reaction chamber having (i) a downstream end in fluid communication with one or more product outlets, and (ii) an upstream end in fluid communication with the downstream end of the second reaction chamber, and (iii) a central axis of the converging section is co-axial to a central longitudinal axis of the second reaction chamber, wherein the gas converging section is defined by a wall surrounding the central axis, wherein the wall of the gas converging section is joined perimetrically with the second reactor wall at the downstream end of the second reaction chamber.

5. The chemical reactor of claim 1, wherein the feed assembly unit comprises:
a. a downstream feed assembly wall, operably connected with the first reactor wall, wherein the downstream feed assembly wall surrounds a central longitudinal axis of the first reaction chamber;
b. an upstream feed assembly wall that is axially spaced upstream from the downstream feed assembly wall and surrounds the central longitudinal axis; wherein the downstream feed assembly wall and the upstream feed assembly wall together defines in part, the mixing chamber for mixing two or more feed streams, wherein the mixing chamber is operably connected to the upstream end of the first reaction chamber; and c. two or more feed inlet flow spaces, each in fluid communication with the mixing chamber, and each configured to inject a feed stream into the mixing chamber at radial and/or non-radial direction with regard to the first central longitudinal axis.

6. The chemical reactor of claim 1, wherein, the distance between any two adjacent gas reactor elements, ranges from 0.5 R to 5 R, wherein 'R' is a radius of a circle, with the plane of the circle being oriented perpendicular to a central axis of the first reaction chamber, and the circle having a maximum radius that can be inscribed within the opening located at the downstream end of the first reaction chamber.

7. The chemical reactor of claim 1, wherein the angle formed between a first central longitudinal axis first reaction chamber and a second central longitudinal axis of the second reaction chamber ranges from 0° to 90°.

8. The chemical reactor of claim 1, further comprising a bottom plate extending across a central longitudinal axis of the second reaction chamber, and located at the upstream end of the second reaction chamber, wherein the bottom plate is joined perimetrically with the second reactor wall.

9. The chemical reactor of claim 1, wherein the second reactor wall has two or more wall openings, each coupled to the opening of a first reaction chamber of a gas reactor element so that two or more second reaction chamber inlets are positioned at the second reactor wall.

10. The chemical reactor of claim 1, wherein the chemical reactor comprises at least 3 gas reactor elements and at most 200 gas reactor elements.

11. The chemical reactor of claim 1, wherein each feed inlet flow space is provided with a circumferentially spaced apart guide vanes, oriented to facilitate a feed stream to flow radially in a spiraling fluid flow pattern, with regard to a central longitudinal axis of the first reaction chamber.

12. The chemical reactor of claim 1, wherein each gas reactor element further comprises a reactor inlet assembly located between the first reaction chamber and the feed assembly unit, wherein the reactor inlet assembly comprises a conduit defined by a circumferential wall surrounding a central longitudinal axis of the first reaction chamber and extending from an upstream end to an opposite downstream end of the conduit, wherein, i) the downstream end of the conduit is in fluid communication with the upstream end of the first reaction chamber, and ii) the upstream end of the conduit is in fluid communication with the mixing chamber, further wherein, the downstream feed assembly wall joins the circumferential wall of the conduit at the upstream end of the conduit and the first reactor wall perimetrically joins the circumferential wall of the conduit at the downstream end of the conduit.

13. The chemical reactor of claim 1, wherein the conduit of the reactor inlet assembly has a circumferential wall of tapering width extending from the downstream end and the upstream end of the conduit, to an annular constricted neck portion, located between the downstream end and the upstream end of the conduit.

14. The chemical reactor of claim 1, wherein each feed inlet flow space is coupled to a manifold configured to inject a feed stream tangentially into the feed inlet flow space.

15. A method of producing chemical products in a chemical reactor comprising (a) two or more gas reactor elements, wherein each reactor element comprises (i) a first reaction chamber and (ii) a feed assembly unit operably connected with the first reaction chamber, each feed assembly unit comprising a mixing chamber and two or more feed inlet flow spaces in communication with the mixing chamber, and (b) a second reaction chamber operably connected to each of the two or more gas reactor elements, the method comprising:

a. introducing two or more feed streams independently in at least two feed inlet flow spaces located in each of the two or more gas reactor elements;

b. mixing the two or more feed streams in the mixing chamber of each gas reactor element, and forming a swirling gas mixture;

c. combusting a portion of the swirling gas mixture and forming a first product stream comprising a mixture of a combustion product stream and a portion of the swirling gas mixture that is not combusted;

d. introducing a portion of the first product stream into the first reaction chamber;

e. subjecting the first product stream present in the first reaction chamber, to a first reaction condition and forming a second product stream;

f. introducing a portion of the second product stream through a second reaction chamber inlet into the second reaction chamber;

g. subjecting two or more second product streams obtained independently from each gas reactor element, to a second reaction condition, and forming a third product stream; and h. removing a portion of the third product stream through one or more product outlets and obtaining the chemical products.

16. The method of claim 15, wherein two or more feed streams comprise at least one hydrocarbon feed stream and at least one non-hydrocarbon feed.

17. The method of claim 15, wherein the first reaction condition and the second reaction condition is a reaction condition suitable for cracking.

18. The method of claim 15, wherein the first reaction condition and the second reaction condition is a reaction condition suitable for pyrolysis.

19. The method of claim 15, wherein the hydrocarbon feed stream is selected from methane, ethane, propane, butane, naphtha, LPG, liquid feed, solid plastic particles, vaporized hydrocarbons having two to thirty carbon atoms, and mixtures thereof.

20. The method of claim 15, wherein the non-hydrocarbon feed stream, is selected from oxygen, hydrogen, steam, carbon dioxide, carbon monoxide, and mixtures thereof.

\* \* \* \* \*